(12) United States Patent
Juhasz et al.

(10) Patent No.: US 10,175,277 B2
(45) Date of Patent: Jan. 8, 2019

(54) IDENTIFICATION OF DEGRADING ELECTRODES IN A MARINE ELECTROMAGNETIC SURVEY SYSTEM

(71) Applicant: PGS Geophysical AS, Lilleaker, Oslo (NO)

(72) Inventors: Andras Robert Juhasz, Kista (SE); Ulf Peter Lindqvist, Kista (SE)

(73) Assignee: PGS Geophysical AS, Oslo (NO)

( * ) Notice: Subject to any disclaimer, the term of this patent is extended or adjusted under 35 U.S.C. 154(b) by 129 days.

(21) Appl. No.: 15/239,628

(22) Filed: Aug. 17, 2016

(65) Prior Publication Data

US 2017/0059502 A1 Mar. 2, 2017

Related U.S. Application Data

(60) Provisional application No. 62/212,182, filed on Aug. 31, 2015.

(51) Int. Cl.
*G01R 27/08* (2006.01)
*G01N 27/04* (2006.01)
(Continued)

(52) U.S. Cl.
CPC .............. *G01R 27/08* (2013.01); *G01N 17/00* (2013.01); *G01N 17/02* (2013.01); *G01N 27/04* (2013.01);
(Continued)

(58) Field of Classification Search
CPC ........ G01R 27/02; G01R 27/20; G01R 27/08; G01V 3/00; G01V 3/15; G01N 27/04; G01N 17/00
(Continued)

(56) References Cited

U.S. PATENT DOCUMENTS

| 2,787,758 A | 4/1957 | Walstrom |
| 3,784,900 A | 1/1974 | Schuster |

(Continued)

FOREIGN PATENT DOCUMENTS

| EP | 0619094 | 12/1994 |
| WO | 8101646 | 6/1981 |

(Continued)

OTHER PUBLICATIONS

Extended European Search Report for European Application No. 16186037.4 dated Jan. 24, 2017.

(Continued)

*Primary Examiner* — Amy He (57) ABSTRACT

A system and method is provided for identifying degrading electrodes in a marine electromagnetic survey system. A system may comprise a sensor array operable for use in a marine electromagnetic survey system, wherein the sensor array comprises a plurality of electrodes. The system may comprise a shunt resistor connected to the electrodes and a processor operable to vary a resistance of the shunt resistor in the presence of a voltage across the electrodes. A method for identifying degrading electrodes may comprise measuring an electric field in a body of water with a pair of electrodes, wherein a shunt resistor is connected between the pair of electrodes. The method may comprise varying a resistance of the shunt resistor. The method may comprise measuring a voltage across the shunt resistor while varying the resistance of the shunt resistor to obtain measured voltages for different shunt resistor values. The method may comprise comparing the measured voltages of the different shunt resistor values to calculate resistance of the pair of electrodes.

26 Claims, 8 Drawing Sheets

(51) Int. Cl.
| | |
|---|---|
| *G01V 3/15* | (2006.01) |
| *G01V 3/00* | (2006.01) |
| *G01N 17/00* | (2006.01) |
| *G01V 3/02* | (2006.01) |
| *G01N 17/02* | (2006.01) |
| *G01V 13/00* | (2006.01) |

(52) U.S. Cl.
CPC .................. *G01V 3/02* (2013.01); *G01V 3/15* (2013.01); *G01V 13/00* (2013.01); *Y02A 90/342* (2018.01); *Y02A 90/344* (2018.01)

(58) Field of Classification Search
USPC ......................................... 324/713, 718, 331
See application file for complete search history.

(56) References Cited

U.S. PATENT DOCUMENTS

| | | | |
|---|---|---|---|
| 3,984,611 A * | 10/1976 | Varrasso | G01R 31/2834 373/40 |
| 4,370,984 A | 2/1983 | Cartmell | |
| 4,406,766 A | 9/1983 | Macdonald | |
| 4,612,094 A | 9/1986 | Davenport et al. | |
| 4,617,518 A | 10/1986 | Srnka | |
| 4,847,980 A | 7/1989 | Witowski et al. | |
| 5,071,537 A | 12/1991 | Yamaguchi et al. | |
| 5,160,590 A | 11/1992 | Totsuka et al. | |
| 5,434,410 A | 7/1995 | Kulwicki | |
| 5,833,825 A | 11/1998 | Otten et al. | |
| 6,674,286 B2 | 1/2004 | Lagmanson | |
| 7,446,535 B1 | 11/2008 | Tenghamn et al. | |
| 7,466,627 B2 | 12/2008 | Karlsen | |
| 7,671,598 B2 | 3/2010 | Ronaess et al. | |
| 7,733,740 B2 | 6/2010 | Hillesund et al. | |
| 7,803,258 B2 | 9/2010 | Sigrist | |
| 7,834,632 B2 | 11/2010 | Tenghamn et al. | |
| 8,131,522 B2 | 3/2012 | Ziolkowski et al. | |
| 8,335,126 B2 | 10/2012 | Sudow et al. | |
| 8,319,497 B2 | 11/2012 | Sudow et al. | |
| 8,472,281 B2 | 6/2013 | Sudow et al. | |
| 8,514,656 B2 | 8/2013 | Juhasz et al. | |
| 8,587,316 B2 | 11/2013 | Juhasz et al. | |
| 8,754,649 B2 | 6/2014 | Sudow et al. | |
| 8,710,845 B2 | 8/2014 | Lindqvist et al. | |
| 8,816,690 B2 | 8/2014 | Sudow et al. | |
| 8,896,313 B2 | 11/2014 | Lindqvist et al. | |
| 9,057,798 B2 | 1/2015 | Juhasz et al. | |
| 8,994,378 B2 | 3/2015 | Juhasz et al. | |
| 9,274,241 B2 | 3/2016 | Lindqvist et al. | |
| 9,372,280 B2 | 6/2016 | Juhasz | |
| 2007/0294036 A1 | 12/2007 | Strack et al. | |
| 2008/0309346 A1 | 12/2008 | MacGregor et al. | |
| 2009/0001985 A1 | 1/2009 | Besson et al. | |
| 2009/0140741 A1 | 6/2009 | Tenghamn | |
| 2009/0294284 A1 | 12/2009 | Hsiung et al. | |
| 2010/0001733 A1 | 1/2010 | Combee | |
| 2010/0225324 A1 | 9/2010 | Strack et al. | |
| 2010/0231224 A1 | 9/2010 | Lindqvist | |
| 2011/0012601 A1 | 1/2011 | Hobbs et al. | |
| 2011/0084696 A1 | 4/2011 | Tenghamn | |
| 2011/0182138 A1 | 6/2011 | Sudow et al. | |
| 2011/0210741 A1 | 9/2011 | Sudow et al. | |
| 2011/0242940 A1 | 10/2011 | Sudow et al. | |
| 2011/0255368 A1 | 10/2011 | Sudow et al. | |
| 2011/0260730 A1 | 10/2011 | Sudow et al. | |
| 2011/0292759 A1 | 12/2011 | Sudow et al. | |
| 2011/0317514 A1 | 12/2011 | Sudow et al. | |
| 2012/0051175 A1 | 3/2012 | Sudow et al. | |
| 2012/0161774 A1 | 6/2012 | Strack et al. | |
| 2013/0162255 A1 | 6/2013 | Sudow et al. | |
| 2013/0166210 A1 | 6/2013 | Sudow et al. | |
| 2013/0187655 A1 | 7/2013 | Juhasz et al. | |
| 2013/0221969 A1 | 8/2013 | Kennedy et al. | |
| 2014/0239958 A1 | 8/2014 | Kennedy et al. | |
| 2014/0253132 A1 | 9/2014 | Juhasz et al. | |
| 2014/0266216 A1 | 9/2014 | Lindqvist et al. | |
| 2015/0153469 A1 | 1/2015 | Sudow et al. | |
| 2015/0035537 A1 | 2/2015 | Juhasz et al. | |
| 2015/0241585 A1 | 8/2015 | Juhasz et al. | |

FOREIGN PATENT DOCUMENTS

| | | |
|---|---|---|
| WO | 99/65389 | 12/1999 |
| WO | 2012106483 | 8/2009 |
| WO | 2012057606 | 5/2012 |

OTHER PUBLICATIONS

Exploration & Production Magazine article for the 2014 Meritorious Awards for Engineering Innovation available from http://www.epmag.com/item/print/2014-Meritorious-Awards-Engineering-Innovation_132699 and http://www.epmag.com dated May 1, 2014.

"Silver chloride electrode", from Wikipedia encyclopedia website: http://en.wikipedia.org/wiki/Silver_chloride_electrode, pp. 1-4, dated Aug. 9, 2011.

Great Britain search report for British application No. GB1301312.3 dated May 9, 2013.

USPTO Office Action for U.S. Appl. No. 13/358,255 dated Aug. 12, 2015.

USPTO Office Action for U.S. Appl. No. 13/358,255 dated Nov. 28, 2014.

USPTO Final Office Action for U.S. Appl. No. 13/358,255 dated Dec. 23, 2015.

USPTO Final Office Action for U.S. Appl. No. 13/358,255 dated Apr. 24, 2015.

USPTO Notice of Allowance for U.S. Appl. No. 13/358,255 dated Mar. 11, 2016.

USPTO Notice of Allowance for U.S. Appl. No. 13/358,255 dated May 26, 2016.

* cited by examiner

IDENTIFICATION OF DEGRADING ELECTRODES IN A MARINE ELECTROMAGNETIC SURVEY SYSTEM

CROSS-REFERENCE TO RELATED APPLICATIONS

The present application claims priority to U.S. Provisional Application No. 62/212,182, filed Aug. 31, 2015, the entire disclosure of which is incorporated herein by reference.

BACKGROUND

The present invention relates generally to the field of marine electromagnetic surveying. Embodiments relate to a system and method for identifying degraded electrodes while the electrodes are deployed in a body of water, such as the sea, within a marine electromagnetic survey system.

Marine electromagnetic surveying may involve towing an energy source at a selected depth in a body of water. One or more survey cables also may be towed in the water at selected depths. The survey cables are essentially long cables which may have electromagnetic sensors disposed thereon at spaced apart locations. The energy source and survey cables may be positioned in the water by attached equipment, such as deflectors and position control devices. Actuation of the energy source may emit an energy field into the body of water. The energy field may interact with the subterranean formations below the water bottom. The change in the energy field due to the interaction with the subterranean formation may be detected by the electromagnetic sensors and used to infer certain properties of the subterranean formation, such as structure, mineral composition and fluid content, thereby providing information useful in the recovery of hydrocarbons. In addition to towed survey cables, marine electromagnetic survey systems may also use sensors that are at a fixed location with respect to the energy source, which may include attachment of electromagnetic sensors on one or more cables positioned on the water bottom and/or attachment of the electromagnetic sensors to one or more subsurface acquisition nodes, for example.

Components used in a marine electromagnetic survey system may include electrodes. For example, electromagnetic sources and electromagnetic sensors may each include a pair of electrodes. When deployed for a marine electromagnetic survey, these electrodes may be exposed to seawater, which may undesirably interact with the surface of the electrodes. For example, because a potential difference may be typically applied across the electrodes during use, the surface of the electrodes may react with the seawater causing undesirable deposits and/or material loss that may degrade electrode performance. In addition, electrode performance may also be degraded by algae and other biological contaminations and/or growths that may occur on the surface of the electrodes. In some instances, the degradation of electrode performance caused by these undesirable interactions may limit the operational life of the electrodes used in the marine electromagnetic survey systems, as the interactions may result in decreased accuracy of measurements from the electrodes, for example, the electrodes may fail during operation. The current techniques for identifying electrodes which may be degrading may be to individually test electrodes above the surface of the water. Drawbacks to this technique for restoring performance may include the time, effort, and expense associated with retrieval and replacement of the electrode above the surface of the water.

Accordingly, there is a need for improved systems and methods for identifying electrodes that are degrading within marine electromagnetic survey systems.

BRIEF DESCRIPTION OF THE DRAWINGS

These drawings illustrate certain aspects of some of the embodiments of the present invention and should not be used to limit or define the invention.

DETAILED DESCRIPTION

The present invention relates generally to the field of marine electromagnetic surveying. Embodiments relate to methods for identifying degrading electrodes while electrodes are deployed in bodies of water, such as the sea, within a marine electromagnetic survey system. A degrading electrode may be defined as an electrode in which the physical, structural, and/or material aspects of the device may over time degrade, be removed, covered, fail, falter, wear off, and/or the like. In examples, electrodes may be exposed to seawater, which may undesirably interact with the surface of the electrode thus causing the electrode to become a degrading electrode. For example, the surface of the electrode may react with the seawater causing undesirable deposits and/or material loss that may degrade electrode performance. Without limitation, algae and other biological contaminations and/or growths may occur on the surface of the electrode. In some instances, the degradation of electrode performance may limit the operational life of the electrode. This may prevent and/or hinder the movement of current and/or voltage through the electrode and thus the sensitivity of the electrode may diminish. The sensitivity of the electrode may be the ability of the electrode to measure and/or record current, voltage, and/or magnetic fields.

Embodiments may be useful for detecting and identifying degrading electrodes while a marine electromagnetic survey system may be in use, thus allowing operators to by-pass a specific electrode and restore electrode performance without requiring out-of-water retrieval and replacement of the electrode. Embodiments may be used to identify degrading electrodes made of various materials including, for example, silver-silver chloride (Ag—AgCl) based electrodes, which may be commonly used in marine electromagnetic survey systems. Electrochemical and/or chemical dissolution of the AgCl layer disposed on the Ag—AgCl-based electrodes may degrade an electrode's performance. Embodiments may be used to locate a single degenerating electrode, within possibly hundreds of electrodes, which may have, for example, such dissolution of the AgCl layer or undesirable deposits and/or other contaminants (e.g., algae and other biological contaminants) that may have built up on the exposed AgCl layer. Identifying degrading electrodes while in use may increase operational efficiency and safety of the marine electromagnetic survey system and may further reduce the time, effort, and expense associated with electrode replacement until the marine electromagnetic survey system has been unloaded on land for scheduled maintenance, at which time the identified degrading electrodes may be replaced. Another option for in-situ improvement of a degraded electrode with damaged and/or removed AgCl layer may be to electrochemically etch away all damaged AgCl and electrochemically to form a new layer. The reactions may be enabled by the presence of ions in seawater.

Figure 1:
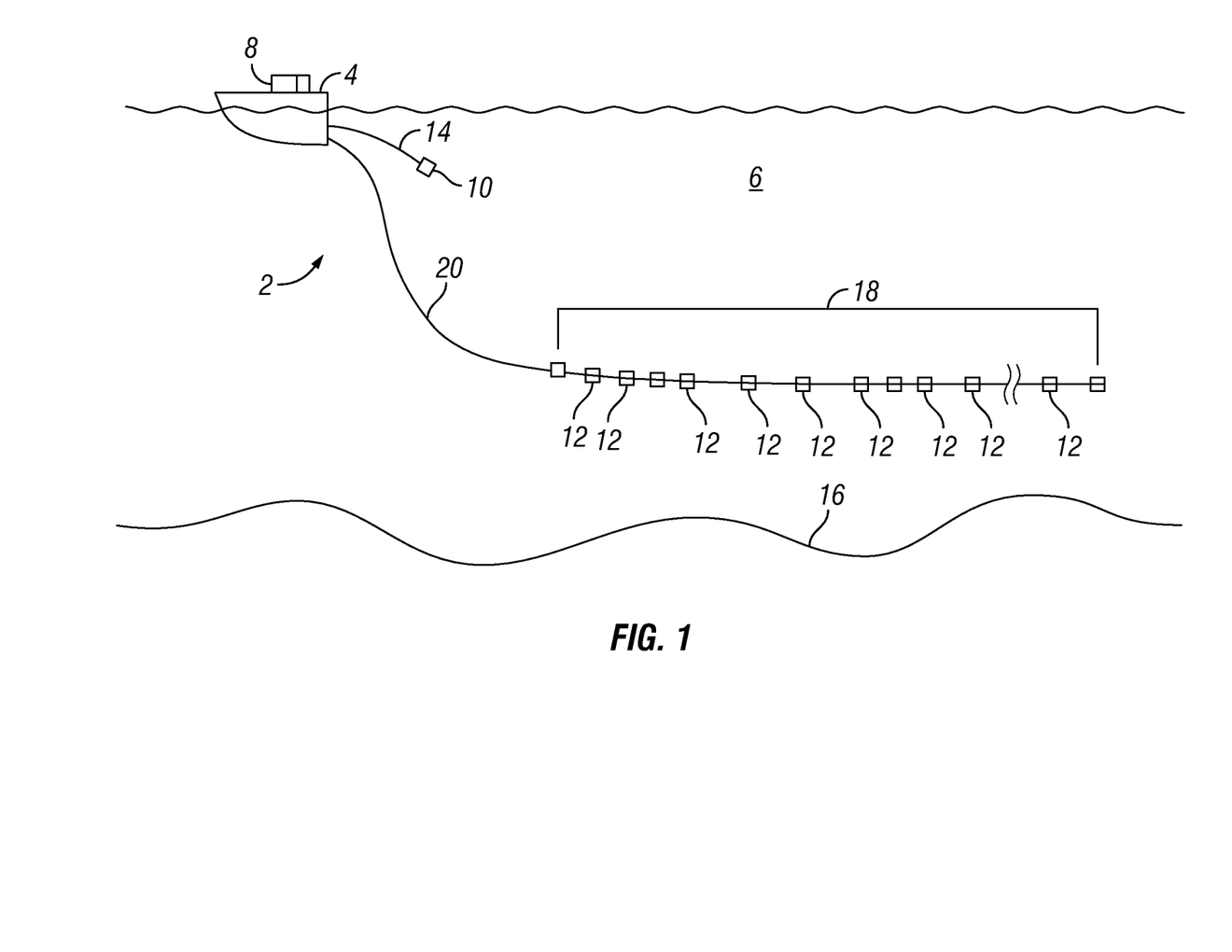
FIG. 1 illustrates an embodiment of a marine electromagnetic survey system.

FIG. 1 illustrates an embodiment of a marine electromagnetic survey system 2. In the illustrated embodiment, marine electromagnetic survey system 2 may include a survey vessel 4 that moves along the surface of a body of water 6, such as a lake or sea. Survey vessel 4 may include thereon equipment, shown generally at 8 and referred to for convenience as a "recording system." Recording system 8 typically includes devices (none shown separately) for navigating survey vessel 4, such as global positioning system ("GPS") receivers, actuating one or more energy sources 10, which may be connected to survey vessel 4 through source cable 14, and recording signals detected by electrodes 12.

Marine electromagnetic survey system 2 may include a plurality of sensor arrays 18 towed by survey vessel 4 (and/or another vessel), which may include electrodes 12 at spaced apart locations. For example, towing a sensor array 18 in a body of water 6, in which sensor array 18 comprises pairs of electrodes. Without limitation, a sensor array 18 may comprise a single cable, or "streamer," operable to be towable in body of water 6 from survey vessel 4 and/or disposable along the ocean floor. Disposed on the single cable may be a single and/or a plurality of electrodes 12, which may be spaced axially along the single cable. In examples, electrodes 12 may be replaced and/or disposed with nodes. Sensor arrays 18 may be towed above water bottom 16. Sensor arrays 18 may be spaced apart laterally, vertically, or both laterally and vertically. "Lateral" or "laterally," in the present context, means transverse to the direction of the motion of survey vessel 4. Sensor arrays 18 may be coupled at their forward end (with respect to the direction of movement of survey vessel 4) to corresponding lead-in lines 20. Each of the lead-in lines 20 may be deployed from survey vessel 4 by a winch or other similar spooling device, which may be used to control the deployed length of lead-in lines 20. It should be noted that, while the present example shows only one sensor array 18, the invention may be applicable to any number of sensor arrays 18 towed by survey vessel 4 or any other vessel.

In some embodiments, sensor array 18 may comprise a plurality of electrodes 12 at spaced apart positions. Sensor array 18 may be operable for use in marine electromagnetic survey system 2. In the illustrated embodiment, sensor array 18 may be located on a single cable, or "streamer," operable to be towable from the survey vessel 4 moving on the surface of the body of water 6. Without limitation, sensor array 18 may be disposed within a cable, and the cable may be disposed along the water bottom. In other embodiments, sensor array 18 may located on multiple streamers displaced horizontally and/or vertically from one another. In alternative embodiments, sensor array 18 may include electrodes 12 located on ocean bottom cables and/or nodes, fixed at or near water bottom 16, either in lieu of or in addition to electrodes 12 on sensor array 18 (or multiple streamers). In still other embodiments, additional electrodes 12 may be located on streamers towed by another vessel (not shown). As another alternative, one or more additional sensor streamers (not shown) may be towed behind survey vessel 4, towed behind another vessel (not shown), located on an ocean bottom cable, or on nodes fixed at or near water bottom 16.

In one embodiment, electrodes 12 may be Ag—AgCl-based electrodes, such as those used for sensor electrodes in marine electromagnetic survey system 2. Those of ordinary skill in the art will appreciate that Ag—AgCl-based electrodes may be fabricated, for example, from sintering of AgCl onto an Ag rod or by chemically or electrochemically treating an Ag surface. In the case of electrochemically treating the surface, the AgCl surface of the electrode may be created by an electrochemical reaction of Ag from the electrode metal with chloride ions in an electrolyte. While a special solution may be typically formulated that contains the chloride ions for the electrochemical treatment, electrodes 12 used in a marine electromagnetic survey system 2 typically may be deployed in seawater, which contains a large amount of chloride ions in accordance with embodiments of the present disclosure. Electrodes may be made of other materials.

Figure 2:
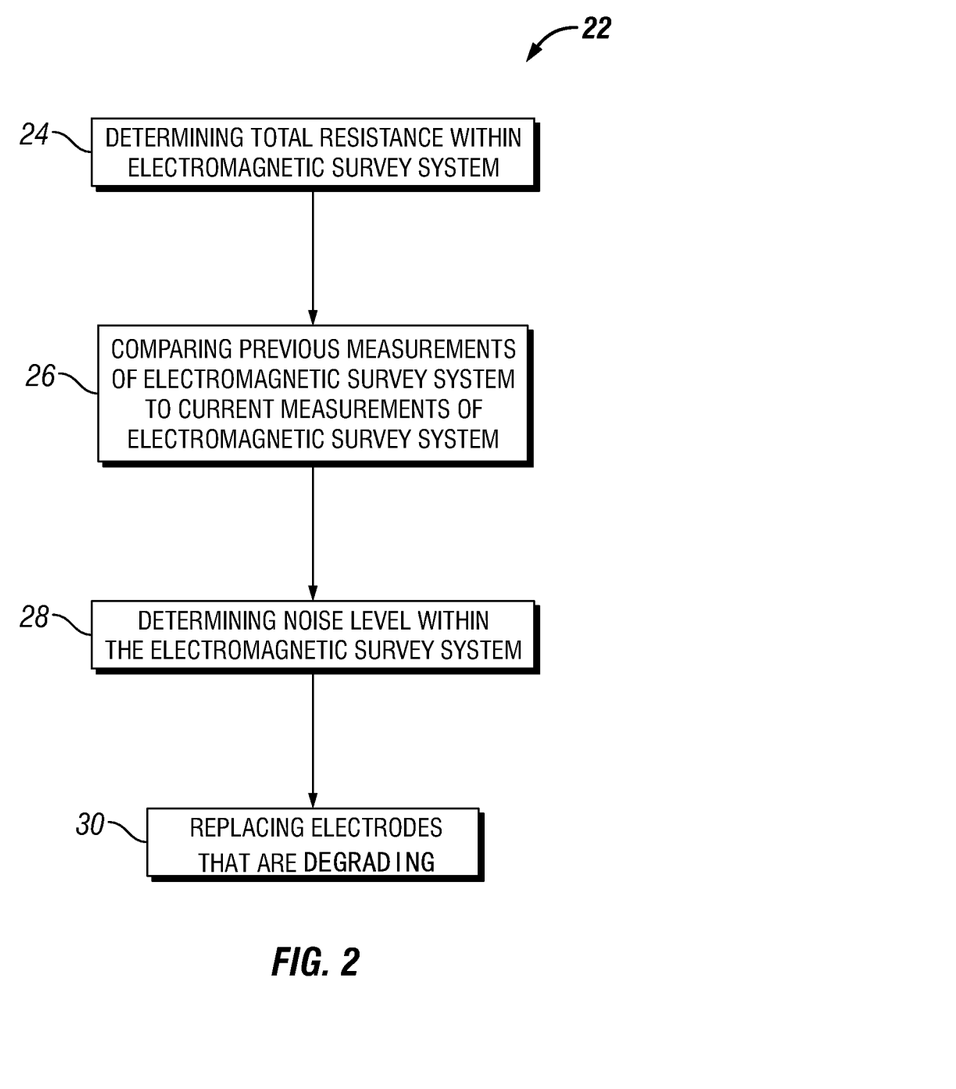
FIG. 2 is a flow chart of a method to identify degrading electrodes.

Referring now to FIG. 2, a flow chart of a method to identify degrading electrodes, identified as method 22, is shown. At step 24, the method 22 may begin with the step of determining a total resistance within a marine electromagnetic survey system 2 (e.g., FIG. 1) for a particular pair of electrodes 12, which may include line (or wire) resistance, electrode resistance (e.g., internal resistance of the pair of electrodes), and water resistance. The pair of electrodes 12 may be selected from the electrodes 12 in the marine electromagnetic survey system 2 shown on FIG. 1. Determining the total resistance to identify a degrading electrode may include measuring an electric field in body of water 6 (e.g., FIG. 1). To measure the electric field, an operator may first measure the voltage over a shunt resistor connected to the pair of electrodes 12. The total resistance may be calculated from this measurement of voltage. Step 24 may include obtaining measurements of voltages across a shunt resistor for different pairs of electrodes from a plurality of electrodes 12. With continued reference to FIG. 2, previous measurements of the total resistance of the marine electromagnetic survey system, at step 26, may be compared to current measurements of the total resistance of the marine electromagnetic survey system. An operator, through a processor, described below, may measure the voltage across the shunt resistor while varying the resistance of the shunt resistor to obtain measured voltages for different shunt resistor values. In examples, the processor may be operable to vary a resistance of the shunt resistor in the presence of a voltage across the pair of electrodes 12. The operator may then compare the different measured voltages of different shunt resistor values to calculate the resistance within a pair of electrodes 12. If changes in total resistance are larger than a limiting (or threshold) value, there may be an issue with one or more of the electrodes 12 in pair. For example, if the change in total resistance exceeds the limiting value, then one (or both) of the electrodes 12 in the pair may be degrading. The limiting value may be selected as a certain increase over an initial or installed value of the total resistance. At step 28, the method 22 may further include determining the noise level within marine electromagnetic survey system 2 for the particular pair of electrodes 12. To determine the noise level within marine electromagnetic survey system 2 for the particular pair of electrodes 12, ambient signals may be recorded when the one or more energy sources (e.g., FIG. 1), such as an electromagnetic source, has been turned off. If the noise level is larger than a limiting value, there may be a problem with one or more electrodes of the pair of electrodes 12. For example, noise levels that exceed the limiting value may indicate that one (or both) of the electrodes in the pair may be degrading. At step 30, the method may further include replacing one or more electrodes that are degrading. The degrading electrodes may have been identified at step 26, for example, where the change in total resistance exceeded a limiting value, or at step 28, for example, where the noise level exceeded a limiting value. At step 30, the method 22 may further include replacing electrodes 12 that are degrading. For example, one or more of the electrodes 12 in the pair of electrodes 12 may be replaced. This may give information regarding whether a single one of the electrodes 12 or the pair of electrodes 12 is degrading. In examples, the pair of electrodes 12 may be disposed within electrode arms (not illustrated) that may comprise many electrode pairs. Method 22 for identifying degrading electrodes may be repeated as many times as necessary to check every possible combination of electrode pairs.

Figure 3:
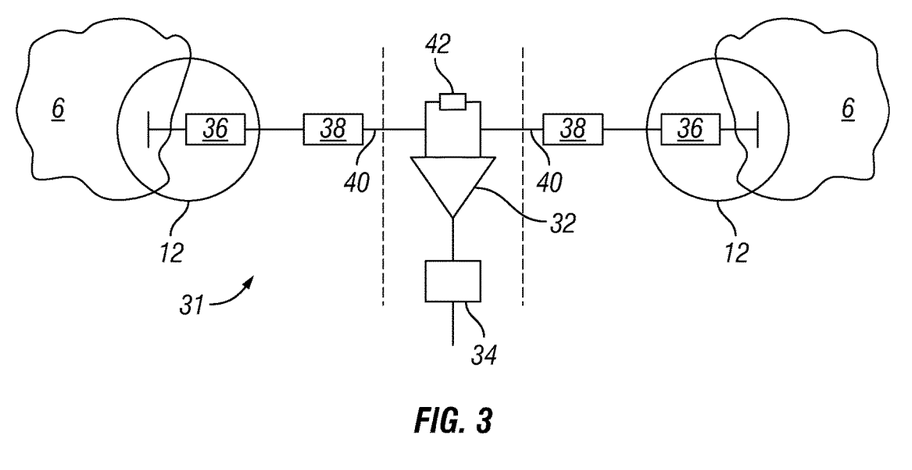
FIG. 3 illustrates an embodiment of a pair of electrodes connected to a system used to measure a voltage between the pair of electrodes.

FIG. 3 illustrates an embodiment of a pair of electrodes 12 connected to a system 31 used to measure a voltage between the pair of electrodes 12. As illustrated, the system 31 may comprise amplifier 32, acquisition and telemetry electronics module 34, and shunt resistor 42. The pair of electrodes 12 shown on FIG. 3 may be selected from the electrodes 12 in the marine electromagnetic survey system shown on FIG. 1. Electrodes 12 may be used to measure an electric field. The electric field in body of water 6 may be determined by measuring the voltage over shunt resistor 42, which is connected between the pair of electrodes 12. In embodiments, an electrical connection within a body of water 6 may be made through a circuit, which may comprise electrodes 12, series resistance 36, line resistance 38, and wires 40, which may connect electrodes 12 to an amplifier 32. Series resistance 36 may represent the internal resistance of the electrodes 12. Measurements of the circuit and its components may determine an electrode 12 that may be degrading. Each component of the circuit may have their own properties which may be measured. As illustrated, electrodes 12 may each have a series resistance 36 that may vary over time due to changes in electrochemical properties on the surface of electrodes 12. Additionally, a line resistance 38 may also be realized as a property of wires 40. In embodiments, wires 40 may comprise a length of about one hundred meters or more, wherein the greater the length of wires 40, the greater line resistance 38 may be. Wires 40 may traverse the length between electrodes 12 and connect electrodes 12 to amplifier 32. In embodiments, amplifier 32 may amplify and transfer a recorded voltage to acquisition and telemetry electronics module 34 for processing. Additionally, a shunt resistance may be disposed at the inputs of amplifier 32, which may provide additional impedance for the whole circuit. Shunt resistance may be described as the electrical load across shunt resistor 42. Shunt resistor 42 may be a device with allows electric current to pass around another point in the circuit by creating a low resistance path. In embodiments, shunt resistor 42 may be used as a measurement point to measure current and voltage before amplifier 32. In other examples, shunt resistor 42 may be used as a bypass of amplifier 32, which may allow electrical current to bypass amplifier 32 if amplifier 32 fails. In embodiments, amplifier 32 amplifies and transfers voltage sensed between two electrodes 12. However, the voltage may never be realized due to environmental factors, current leaks in circuity, and other unknown elements. Therefore, an actual potential voltage between two electrodes 12 may be found through measurements of resistance and other devices. To determine the actual potential voltage between two electrodes 12, within body of water 6 from the voltage, Equation 1, shown below, may be used.

$$V_A = V \times \frac{R_L}{R_{E1} + R_{W1} + R_L + R_{E2} + R_{W2}} \quad (1)$$

When measuring the resistance in the circuit, at certain intervals, shunt resistor 42 may be varied by connecting other shunt resistors (not illustrated) in parallel with shunt resistor 42, which may result in several readings of voltage input into amplifier 32. In embodiments, if more than two values of shunt resistor 42 are used, an average value may be formed. In examples, the average value of shunt resistors 42 may be obtained by performing a mathematical operation of a least squares fit to Equation 1, which may relate the voltage V and shunt resistor values. In Equation 1, $V_A$ represents the voltage across amplifier 32, V represents the measured voltage, $R_L$ represents shunt resistor 42, $R_{E1}$ and $R_{E2}$ represent series resistance 36, and $R_{W1}$ and $R_{W2}$ represent line resistance 38. Additionally, for varying the value of shunt resistor 42, a series resistor (not illustrated) may be introduced in addition to the existing shunt resistor 42. Taking measurements of voltage across shunt resistor 42 while varying the resistance of shunt resistor 42 may provide different voltage measurements across different shunt resistors 42. The measured voltages from different shunt resistor 42 may be used to calculate the resistance of a pair of electrodes 12. In examples, a multiplexer 52, referring to FIG. 4, may connect a pair of electrodes 12 in sensor array 18 to an amplifier 32. The resistance from the series resistor may be similar to shunt resistor 42, which may produce a significant voltage difference within the circuit. In embodiments, the shunt resistor 42 may be selected to match the expected variations in electrodes 12 and line resistances 38.

Figure 4:
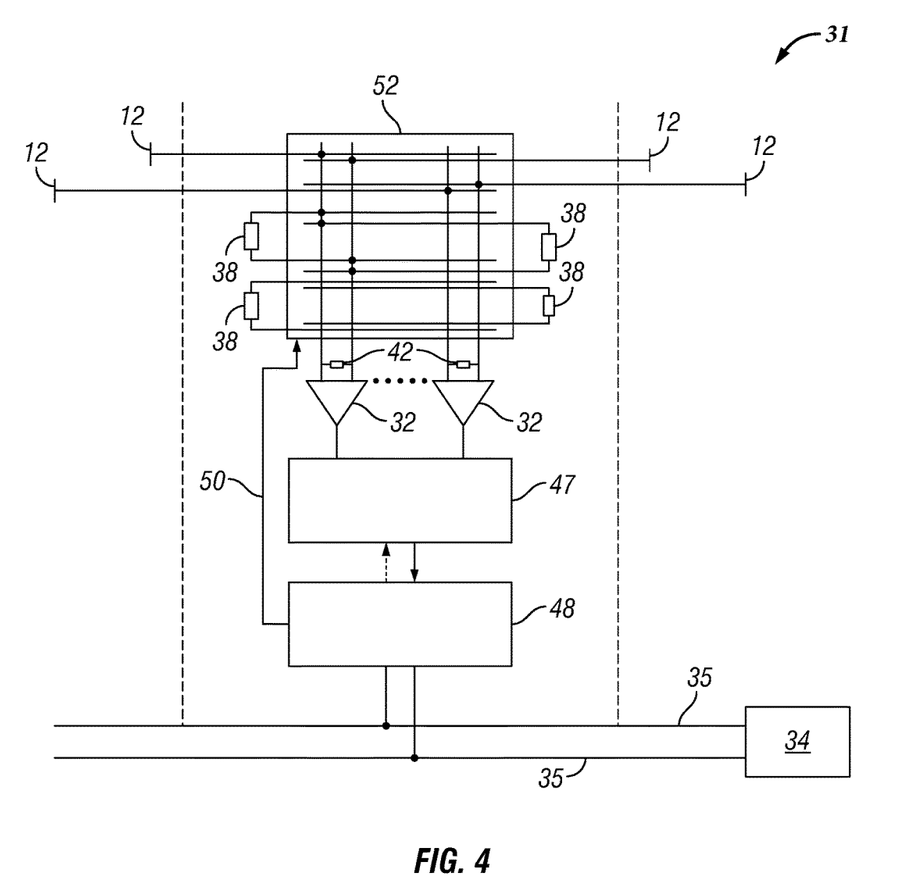
FIG. 4 illustrates an embodiment of a system to measure the voltage between two or more pairs of electrodes.

Referring to FIG. 4, another embodiment of system 31 to measure the voltage between two or more pairs of electrodes 12 is shown. As illustrated, system 31 may further comprise analog-to-digital converter 47, processor 48, and multiplexer 52. In the illustrated embodiment, multiplexer 52 may be implemented to test electrodes 12 and identify which electrodes 12 may be degrading. As illustrated, pairs of electrodes 12 may be connected to rows and/or columns of the multiplexer 52 together with different shunt resistors 42. In examples, this may allow for changing connection of the multiplexer 52 from a first pair of electrodes 12 to a second pair of electrodes 12. Additionally, any number of amplifiers 32, with corresponding shunt resistors 42, may be connected to column outputs of multiplexer 52. As illustrated, amplifiers 32 may be connected to an analog-to-digital converter 47. Analog-to-digital converter 47 may convert analog signals to digital signals for processing by a processor 48. Without limitation, amplifier 32 may be connected to analog-to-digital converter 47 and analog-to-digital converter 47 may be connected to processor 48. In embodiments, processor 48 may control, through a control line 50, connections between different electrodes 12 within multiplexer 52 and amplifiers 32. Without limitation, processor 48 may be operable to change the multiplexer connection from the pair of electrodes 12 to a second pair of electrodes in sensor array 18. Processor 48 may be able to change, vary, and/or add a connection on multiplexer 52 and thus control the connection within multiplexer 52 between a first and second pair of electrodes 12. Processor 48 may be able to change, vary, and/or add a connection on multiplexer 52 at various time intervals, including, without limitation, intervals ranging from about once every half second to about once every five seconds, about once every one second to about once every ten seconds, about once every fifty milliseconds to about once every five seconds, about once every second to about once every three hundred seconds, about once every one hundred seconds to about once every four hundred seconds, about once every two hundred seconds to about once every three hundred seconds, or about once every thirty seconds to about once every three hundred seconds. In embodiments, processor 48 may be able to change, vary, and/or add a connection on multiplexer 52 at about once every two hundred seconds or about once every one second. At a set time, processor 48 may change the configuration of multiplexer 52 between different electrodes 12, which may allow for acquisition and telemetry electronics module 34 to check additional electrodes 12. This process may be repeated any number of times and in any order, to identify degrading electrodes 12 along sensor array 18. In embodiments, processor 48 may connect at least two resistors in parallel with at least two electrodes 12, an amplifier 32, and associated shunt resistor 42 within multiplexer 52. Information received from analog-to-digital converter 47 may move from processor 48 to telemetry lines 35, which may transmit the information to acquisition and telemetry electronics module 34. This set up may allow acquisition and telemetry electronics module 34 to determine actual potential voltage, which may allow for the determination and identification of an electrode 12 which may be degrading. Additional methods may also be implemented to identify electrodes 12 that may be degrading within multiplexer 52. For example, changing line resistance 38 of multiplexer 52, may change the resistance of the shunt resistor and the resistance to amplifiers 32. Varying the shunt resistance may help produce more equations to determine the internal and external resistances of multiplexer 52.

With continued reference to FIG. 4, by selection of the shunt resistance for the shunt resistors 42, sixteen different load values may be obtained, which may enable a creation of a load "waveform" that may be suitable for frequency domain processing, such as simple square wave to approximations of sine-waves, triangular waves, and/or pseudo-random binary sequences. Furthermore, the voltage that is measured by system 31 may be the standard acquisition waveform and/or a specially designed waveform. In some embodiments, the standard acquisition waveform and a higher frequency switching of shunt resistors 42 may enable frequency domain processing and fully continuous characterization of the voltage. For example, if the geophysical content of the measurement signal may be in the 0-10 Hz region, the shunt resistors 42 may be switched at 20 Hz. To circumvent the fact that the whole circuit and a pair of two electrodes 12 may be characterized at once, different combinations of pairs of the electrodes 12 may be measured. For example, one of the electrodes 12 may be measured in a pair with different ones of electrodes 12 attached to sensor array 18 (e.g., FIG. 1) to pinpoint a whether one or more of electrodes 12 is degrading.

Figure 5:
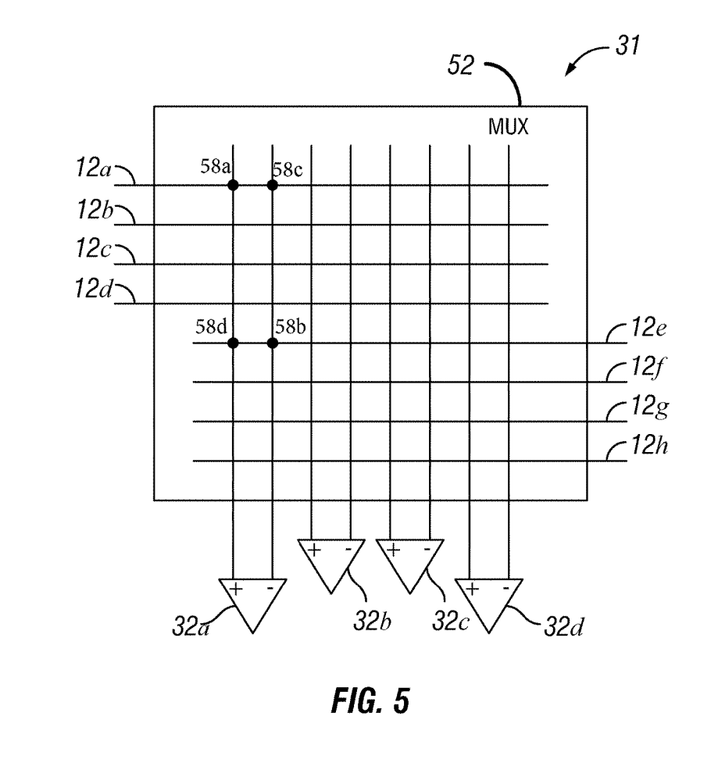
FIG. 5 illustrates another embodiment of a system to measure the voltage between two or more pairs of electrodes.

Referring now to FIG. 5, another embodiment of a system 31 to measure the voltage between two or more pairs of electrodes 12a-12h is shown. As illustrated, system 31 may include multiplexer 52 that may be used to connect pairs of electrodes 12a-12h in different configurations to amplifiers 32a-32d. In some embodiments, connections points 58a-58d within multiplexer 52 may be changed, thus changing connections between electrodes 12a-12h and the line resistance 38 (e.g., FIG. 3). Resulting voltage measurements may be analyzed to identify whether one or more of electrodes 12a-12h may be degrading.

Figure 6:
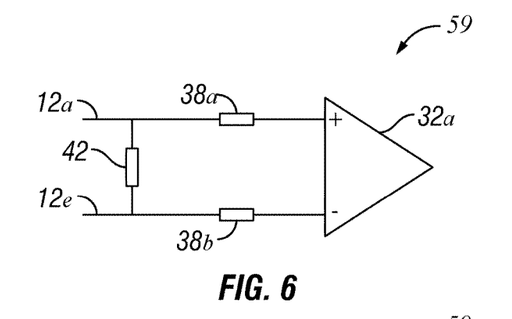
FIG. 6 is a diagram illustrating a circuit that may be formed using the system of FIG. 5.
Figure 7:
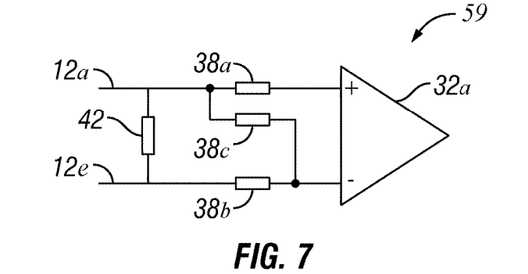
FIG. 7 is a diagram illustrating another circuit that may be formed using the system of FIG. 5.
Figure 8:
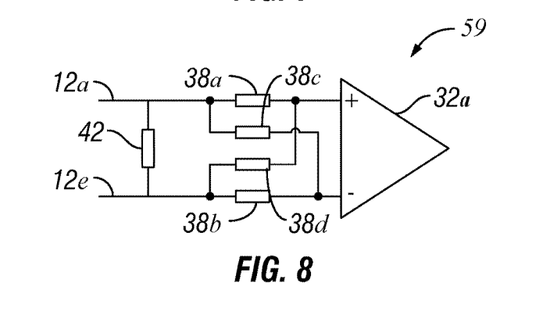
FIG. 8 is a diagram illustrating another circuit that may be formed using the system of FIG. 5.

FIGS. 6-8 are diagrams illustrating different circuits 59 that may be formed using the multiplexer 52 shown on FIG. 5 to connect various combinations of electrodes 12a-12h to one of amplifiers 32. FIG. 6 is a diagram illustrating the circuit 59 formed when multiplexer 52 (e.g., FIG. 5) is used to connect electrodes 12a and 12e to amplifier 32a by way of connections points 58a and 58b (e.g., FIG. 5). As illustrated on FIG. 6, the circuit 59 may comprise line resistances 38a and 38b between each of electrodes 12a and 12a and amplifier. Line resistance 38a represents the line resistance 38a from connection point 58a, and line resistance 38b represents the line resistance 38b from connection point 58 between each of electrodes 12a and 12e and amplifier 32a. FIG. 7 is a diagram illustrating the circuit 59 formed when multiplexer 52 (e.g., FIG. 5) is used to connect electrodes 12a and 12e to amplifier 32a by way of connections points 58a, 58b, and 58c (e.g., FIG. 5). As illustrated on FIG. 7, the circuit 59 may comprise line resistances 38a, 38b, and 38c between each of electrodes 12a and 12a and amplifier 32a. Line resistance 38c represents an additional line resistance 38c from connection point 58c, which may function as a shunt resistance in parallel. FIG. 8 is a diagram illustrating the circuit 59 formed when multiplexer 52 (e.g., FIG. 5) is used to connect electrodes 12a and 12e to amplifier 32a by way of connections points 58a, 58b, 58c, and 58d (e.g., FIG. 5). As illustrated on FIG. 8, the circuit 59 may comprise line resistances 38a, 38b, 38c, and 38d between each of electrodes 12a and 12a and amplifier 32a. Line resistance 38d represents an additional line resistance 38d from connection point 58d, which may function as a shunt resistance in parallel. This embodiment shown on FIG. 8 may lower provide lower effective shunt resistance due to line resistance 38c and line resistance 38d are both in parallel with line resistance 38a and line resistance 38b, which may help in the identification of electrodes 12 which may be degrading. While not present in system 31 shown on FIG. 5, shunt resistor 42 is shown on FIGS. 6-8 as the different circuits 59 may create a psuedo shunt resistance at the inputs of amplifier 32a.

Figure 9:
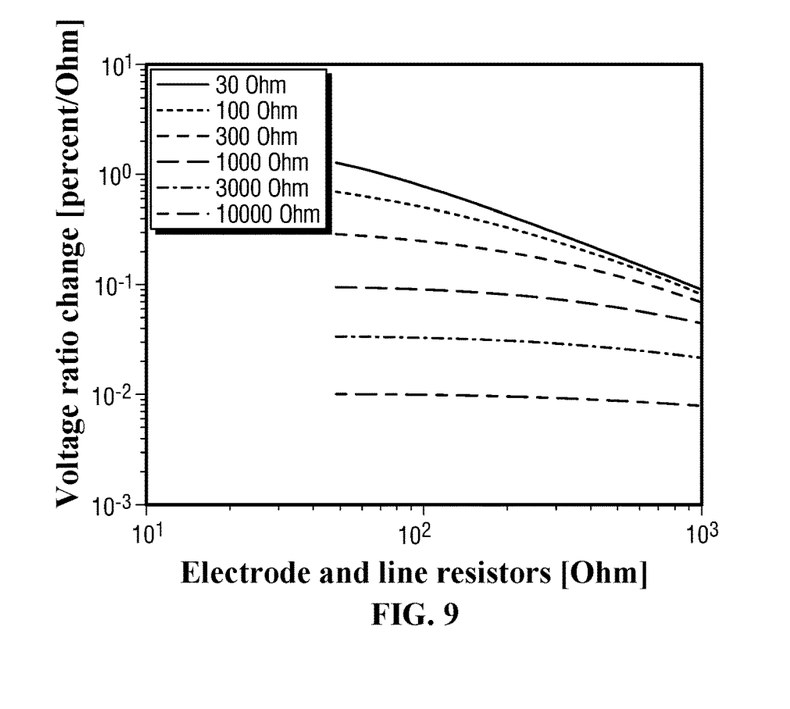
FIG. 9 is a graph illustrating the relationship between the average of the voltage ratio change and the internal electrode and line resistance.
Figure 10:
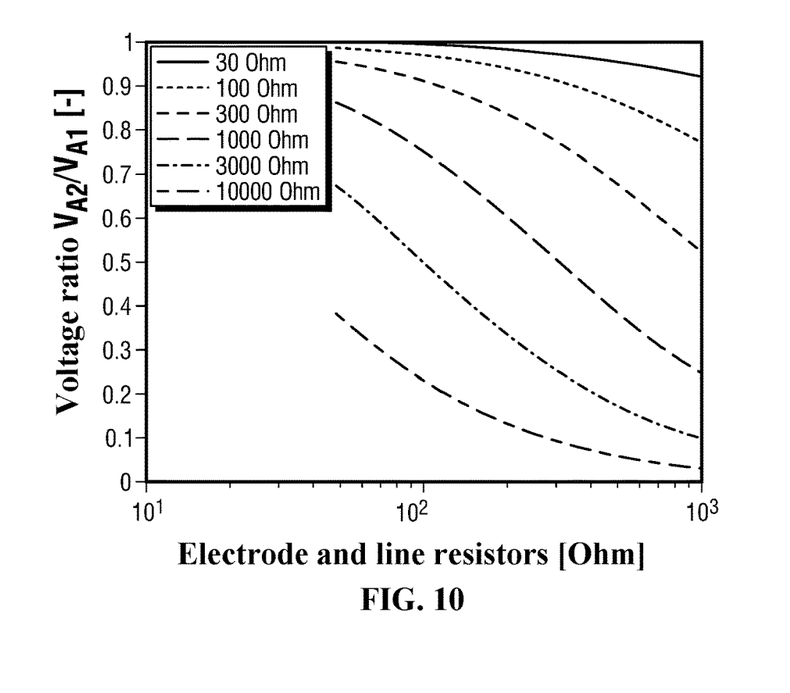
FIG. 10 is a graph illustrating the relationship between the voltage ratio and the internal electrode and line resistance.

FIGS. 9 and 10 are graphs showing the results of simulations where the shunt resistance was varied. In the simulations, the actual potential voltage (Va) was calculated both before and after additional shunt resistance was added. For the simulations, the additional shunt resistance (30-10000 ohm) was added in parallel to an already existing shunt resistance of 10,000 ohm. FIG. 9 illustrates the voltage ratio as a function of a total of the internal electrode resistance (e.g., series resistance 36 on FIG. 3) and line resistance (e.g., line resistance 38 on FIG. 3). Voltage ratio is defined as the ratio of actual potential voltage ($Va_1$) before adding an additional shunt resistance and actual potential voltage (Va$_2$) after adding an additional shunt resistance. FIG. 10 illustrates the voltage ratio change as a function total of the internal electrode resistance (e.g., series resistance 36 on FIG. 3) and line resistance (e.g., line resistance 38 on FIG. 3). Voltage ratio change is defined as the voltage ratio per 1 ohm change in the internal electrode and line resistance. If the internal electrode and line resistance is increased by 1 ohm, this will increase the voltage ratio by slightly less than 1% if the initial line and electrode resistance is 100 ohm. If an additional shunt resistance of 100 ohm is added, a voltage ratio change of less 0.5 may be exhibited. As illustrated on FIGS. 9 and 10, it may be desired for the additional shunt resistance to be less than 1 kilo-ohm.

As previously described, embodiments may be used for identifying whether one or more of electrodes 12 may be degrading while deployed in body of water 6 with a marine electromagnetic survey system 2. For example, embodiments may be used to identify one or more of electrodes 12 which are degrading that are installed on a towed sensor array 18, as shown in FIG. 1. As will be described below, in alternative embodiments, electrodes 12 may attached to one or more subsurface acquisition nodes 62 (FIG. 11), or electrodes 12 may be attached on one or more cables 66 positioned on (or near) water bottom 16 (FIG. 12).

Figure 11:
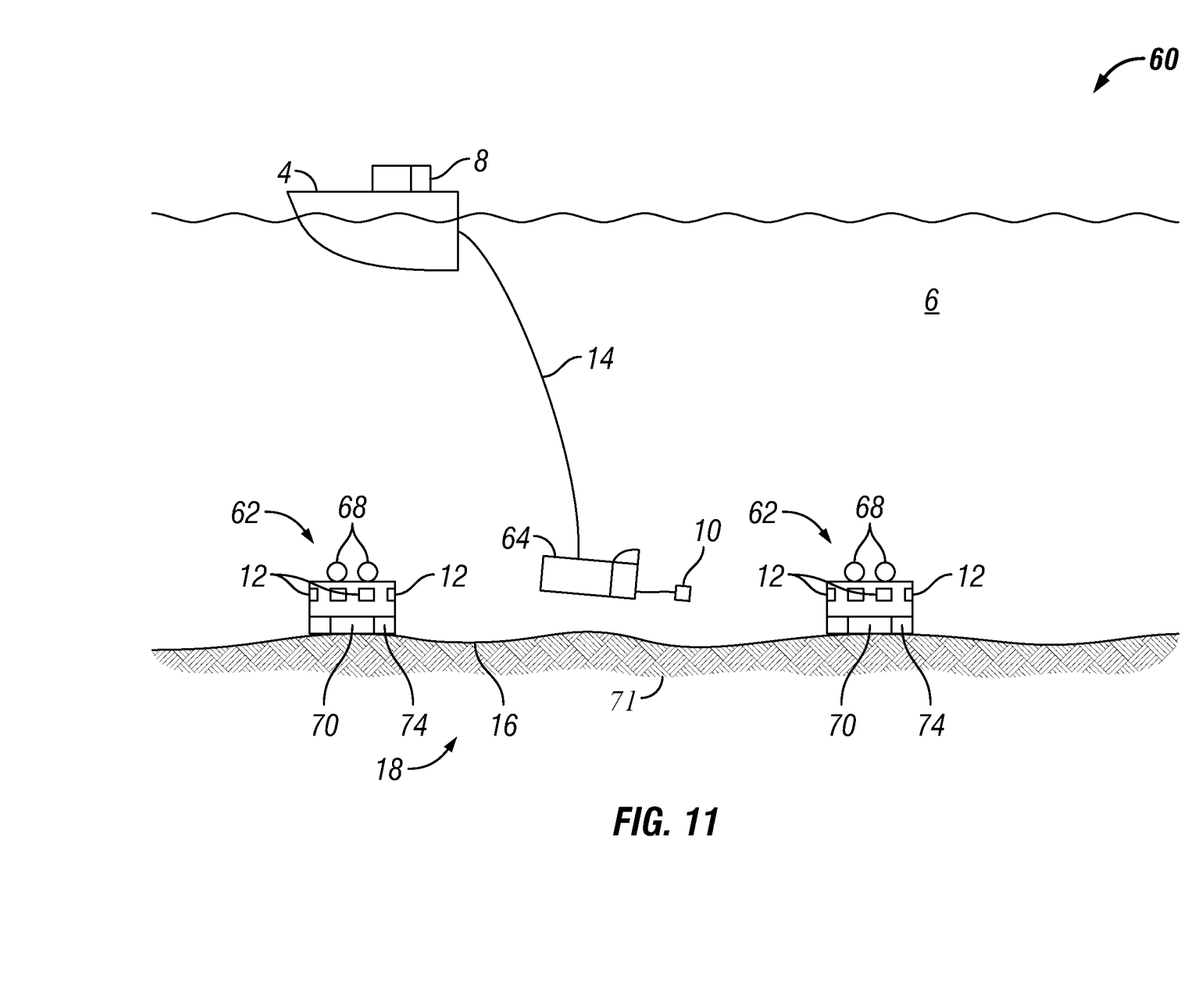
FIG. 11 illustrates an embodiment of an another marine electromagnetic survey system.

FIG. 11 illustrates a marine electromagnetic survey system 60 that includes electrodes 12 installed on subsurface acquisition nodes 62. In the illustrated embodiment, marine electromagnetic survey system 60 includes a survey vessel 4 that moves along the surface of body of water 6. Survey vessel 4 generally may include a recording system 8. A submersible vehicle 64 carrying an energy source 10 may be attached to survey vessel 4 by source cable 14. One or more subsurface acquisition nodes 62 may be located on water bottom 16. A sensor array 18 may comprise at least two subsurface acquisition nodes 62. Although the embodiment shown in FIG. 11 shows two subsurface acquisition nodes 62 and one energy source 10, it is to be understood that the number of such subsurface acquisition nodes 62 and energy source 10 may not be limited on the scope of the invention. Other configurations may include more or fewer subsurface acquisition nodes 62 and energy sources 10. Each of the subsurface acquisition nodes 62 may include a flotation device 68, a ballast weight (not illustrated,) and electromagnetic sensors 70. Electromagnetic sensors 70 may generate response signals, such as electrical or optical signals, in response to detecting energy emitted from the energy source 10 after the energy has interacted with rock formations 71 below water bottom 16. As illustrated, the electromagnetic sensors 70 may include electrodes 12 and electronics module 74. Electronics module 74 may be used to record the voltage differentials across electrodes 12. As described above, electrodes 12 may be degrading on subsurface acquisition nodes 62. Shunt resistors 42 (e.g., FIG. 3) may be disposed within the circuitry connecting electrodes 12 and electronics module 74, which may help in the determination of electrodes 12 which may be degrading. Determination of electrodes 12 that may be degrading may prevent recorded signals from being skewed and/or corrupted during processing of recorded signals.

Figure 12:
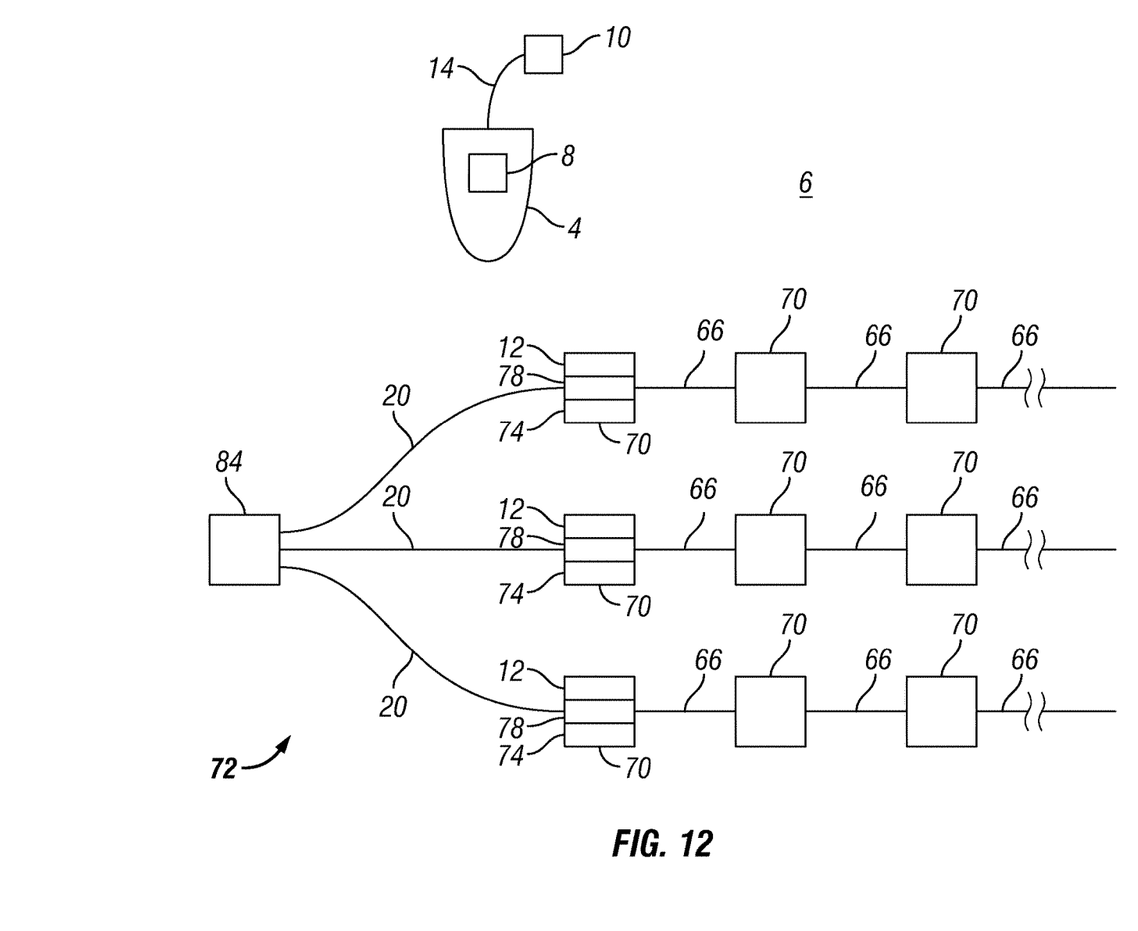
FIG. 12 illustrates an embodiment of yet another marine electromagnetic survey system.

FIG. 12 illustrates an embodiment of a marine electromagnetic survey system 72 that includes electromagnetic sensors 70 installed on one or more cables 66 disposed along a water bottom 16 (shown on FIG. 3). In the illustrated embodiment, marine electromagnetic survey system 72 includes a survey vessel 4 that moves along the surface of body of water 6. Survey vessel 4 generally may include a recording system 8 and tow one or more energy sources 10 through source cable 14. As illustrated, electromagnetic sensors 70 include electrodes 12, switches 78, and electronics module 74, although other components may also be included. Electromagnetic sensors 70 may generate response signals, such as electrical or optical signals, in response to detecting energy emitted from energy source 10 after the energy has interacted with rock formations (not illustrated) below water bottom (not illustrated). Switches 78 may be programed to change between different electrodes 12 to facilitate in the detection of degrading electrodes. As described above, electrodes 12 may degrade within electromagnetic sensors 70. Shunt resistors 42 (e.g., FIG. 3), may be disposed within the circuitry of electromagnetic sensors 70 (or at another position on cables 66), which may help in the determination of which electrodes 12 may be degrading. Determination of electrodes 12 that may be degrading may prevent recorded signals from being skewed and/or corrupted during processing of the signals. The signals gathered by the electromagnetic sensors 70, through electrodes 12, may be communicated along cables 66 to recording buoy 84, which may be, for example, electrically coupled to the electromagnetic sensors 70 by lead-in lines 20. Although the embodiment shown in FIG. 12 shows three cables 66 each with a respective lead-in line 20 all of which are coupled to buoy 84, it is to be understood that the number of such cables 66, lead-in lines 20, and buoy 84 may be different in various embodiments. Other configurations may include more or fewer cables 66, lead-in lines 20, and buoys 84.

The particular embodiments disclosed above are illustrative only, as the described embodiments may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. All numbers and ranges disclosed above may vary by some amount. Whenever a numerical range with a lower limit and an upper limit is disclosed, any number and any included range falling within the range are specifically disclosed. Moreover, the indefinite articles "a" or "an," as used in the claims, are defined herein to mean one or more than one of the element that it introduces. Also, the terms in the claims have their plain, ordinary meaning unless otherwise explicitly and clearly defined by the patentee. If there is any conflict in the usages of a word or term in this specification and one or more patent or other documents that may be incorporated herein by reference, the definitions that are consistent with this specification should be adopted for the purposes of understanding this invention.

What is claimed is:

1. A system for identifying degrading electrodes in a marine electromagnetic survey system, comprising:
    a sensor array operable for use in the marine electromagnetic survey system, wherein the sensor array comprises a plurality of electrodes;
    a shunt resistor connected to at least one pair of electrodes from the plurality of electrodes, wherein the shunt resistor comprises a variable resistance; and
    a processor operable to vary the variable resistance of the shunt resistor in the presence of a voltage across the electrodes to determine a degrading electrode.

2. The system of claim 1, further comprising telemetry lines, wherein the telemetry lines connect the processor to an acquisition and telemetry electronics module for processing.

3. The system of claim 1, wherein the processor is operable to control a connection within a multiplexer.

4. The system of claim 3, wherein the multiplexer connects the at least one pair of electrodes from the plurality of electrodes to an amplifier.

5. The system of claim 4, wherein the amplifier is connected to an analog-to-digital converter and the analog-to-digital converter is connected to the processor.

6. The system of claim 4, wherein the processor is operable to change the connection in the multiplexer from the at least one pair of electrodes to a second pair of electrodes from the plurality of electrodes.

7. The system of claim 1, wherein sensor array is disposed within a streamer operable to be towed in a body of water.

8. The system of claim 1, wherein the sensor array is disposed within a subsurface acquisition node or on a cable disposed along a water bottom.

9. A method for identifying degrading electrodes, comprising:
measuring an electric field in a body of water with a pair of electrodes, wherein a shunt resistor is connected between the pair of electrodes;
varying a resistance of the shunt resistor;
measuring a voltage across the shunt resistor while varying the resistance of the shunt resistor to obtain measured voltages for different shunt resistor values; and
comparing the measured voltages of the different shunt resistor values to calculate resistance of the pair of electrodes.

10. The method of claim 9, further comprising calculating a change in total resistance for the pair of electrodes and comparing the change in total resistance to a limiting value to identify degrading electrodes, wherein the total resistance comprises line resistance, electrode resistance, and water resistance.

11. The method of claim 9, further comprising identifying one of the pair of electrodes as a degrading electrode, and replacing the degrading electrode with another electrode in the step of measuring the electric field.

12. The method of claim 9, further comprising deten lining a first actual potential voltage between a first electrode and a second electrode, wherein the first electrode and the second electrode are the pair of electrodes.

13. The method of claim 12, further comprising determining a second actual potential voltage between the first electrode and a third electrode and comparing the first actual potential voltage to the second actual potential voltage to identify degrading electrodes from the first electrode, the second electrode, and the third electrode.

14. The method of claim 13, further comprising repeating the method and alternating between a plurality of electrodes continuously to identify degrading electrodes.

15. The method of claim 9, wherein the pair of electrodes are connected to a row or a column of a multiplexer.

16. The method of claim 15, further comprising changing connection of the multiplexer from the pair of electrodes to a second pair of electrodes.

17. The method of claim 16, wherein the connection is changed in the multiplexer about once every thirty seconds to about once every three hundred seconds.

18. The method of claim 16, wherein the connection is changed in the multiplexer about once every fifty milliseconds to about once every five seconds.

19. The method of claim 9, further comprising changing an internal resistance within a multiplexer to change the resistance of the shunt resistor.

20. The method of claim 9, further comprising towing a sensor array in the body of water, wherein the sensor array comprises the pair of electrodes.

21. A method comprising:
deploying a plurality of electrodes in a body of water;
obtaining measurements of voltages across a shunt resistor for different pairs of electrodes from the plurality of electrodes, wherein the shunt resistor comprises a variable resistance; and
identifying one or more degrading electrodes from the plurality of electrodes based, at least in part, in the measurements of voltages.

22. The method of claim 21, wherein the deploying comprises towing the plurality of electrodes in the body of water.

23. The method of claim 21, further comprising varying the variable resistance of the shunt resistor.

24. The method of claim 21, wherein the identifying one or more degrading electrodes from the plurality of electrodes comprises calculating a change in total resistance for a particular one of the different pairs of electrodes, and comparing the change in total resistance to a limiting value to identify degrading electrodes, wherein the total resistance comprises line resistance, electrode resistance, and water resistance.

25. The method of claim 21, wherein the identifying one or more degrading electrodes from the plurality of electrodes comprises deteiinining a noise level for measurements with a particular one of the different pairs of electrodes, and comparing the noise level to a limiting value to identify degrading electrodes.

26. A method comprising:
deploying a plurality of electrodes in a body of water;
obtaining measurements of voltages across a shunt resistor for different pairs of electrodes from the plurality of electrodes; and
identifying one or more degrading electrodes from the plurality of electrodes based, at least in part, in the measurements of voltages, wherein the identifying one or more degrading electrodes from the plurality of electrodes comprises determining a noise level for measurements with a particular one of the different pairs of electrodes, and comparing the noise level to a limiting value to identify degrading electrodes.

* * * * *